United States Patent [19]

Fonger et al.

[11] Patent Number: 5,522,834
[45] Date of Patent: Jun. 4, 1996

[54] INTERNAL MAMMARY ARTERY CATHETER AND METHOD

[75] Inventors: James D. Fonger, Wayland, Mass.; Mark P. Ashby, Laguna Niguel, Calif.

[73] Assignee: Applied Medical Resources Corporation, Laguna Hills, Calif.

[21] Appl. No.: 339,638

[22] Filed: Nov. 14, 1994

Related U.S. Application Data

[63] Continuation of Ser. No. 962,975, Oct. 15, 1992, abandoned.

[51] Int. Cl.⁶ .................................................. A61M 29/00
[52] U.S. Cl. .................................................. 606/194; 604/96
[58] Field of Search .................................. 606/191–195, 606/8, 215, 216, 152–153; 604/49–53, 96–104; 128/898; 623/1; 600/36

[56] References Cited

U.S. PATENT DOCUMENTS

| | | |
|---|---|---|
| 3,435,826 | 5/1964 | Fogarty . |
| 3,978,863 | 9/1976 | Fettel et al. .............................. 606/192 |
| 4,276,874 | 7/1981 | Wolvek et al. ........................... 604/96 |
| 4,307,722 | 12/1981 | Evans ....................................... 606/194 |
| 4,311,133 | 1/1982 | Robinson . |
| 4,315,512 | 2/1982 | Fogarty . |
| 4,318,410 | 3/1982 | Chin ........................................ 606/194 |
| 4,327,709 | 5/1982 | Hanson et al. ........................... 604/96 |
| 4,351,341 | 9/1982 | Goldberg et al. ........................ 604/97 |
| 4,444,188 | 4/1984 | Bazell . |
| 4,493,711 | 1/1985 | Chin et al. ............................... 606/192 |
| 4,552,127 | 11/1985 | Schiff ...................................... 606/192 |
| 4,564,014 | 1/1986 | Fogarty . |
| 4,614,188 | 9/1986 | Bazell . |
| 4,721,507 | 1/1988 | Chin ....................................... 606/194 |
| 4,734,093 | 3/1988 | Bonello et al. ......................... 606/194 |
| 4,820,283 | 4/1989 | Schickling . |
| 4,909,258 | 3/1990 | Kuntz . |
| 4,968,300 | 11/1990 | Moutafis . |
| 5,007,919 | 4/1991 | Silva et al. .............................. 606/194 |
| 5,078,727 | 1/1992 | Hannam et al. ......................... 606/194 |
| 5,087,246 | 2/1992 | Smith . |
| 5,141,518 | 8/1992 | Hess et al. .............................. 606/194 |
| 5,192,290 | 3/1993 | Hilal ....................................... 606/194 |
| 5,209,727 | 5/1993 | Radisch, Jr. et al. ................... 606/194 |

FOREIGN PATENT DOCUMENTS 0592182  7/1925  France ................................. 606/191

OTHER PUBLICATIONS

"An Improved Technique for Internal Mammary Artery Graft Preparation;" by Thomas J. Fogarty, M.D., et al.

Primary Examiner—C. Fred Rosenbaum
Assistant Examiner—Mark Bockelman
Attorney, Agent, or Firm—Richard L. Myers

[57] ABSTRACT

A catheter includes a hub and a stylet extending through the hub to a distal end of the catheter. A balloon fixed at its proximal end to the hub and at its distal end to the stylet is axially extendible by operation of the stylet. Inserting the catheter, in its extended state, into an arterial conduit enables the balloon to be inflated and to exert only radial forces against the interior of the vessel. This apparatus and procedure overcomes spasms normally associated with preparation of an arterial conduit, such as the internal mammary artery, for bypass surgery. Extension of the balloon to as much as six times its initial length can be accomplished by positioning a separation spring between the stylet and the balloon.

9 Claims, 3 Drawing Sheets

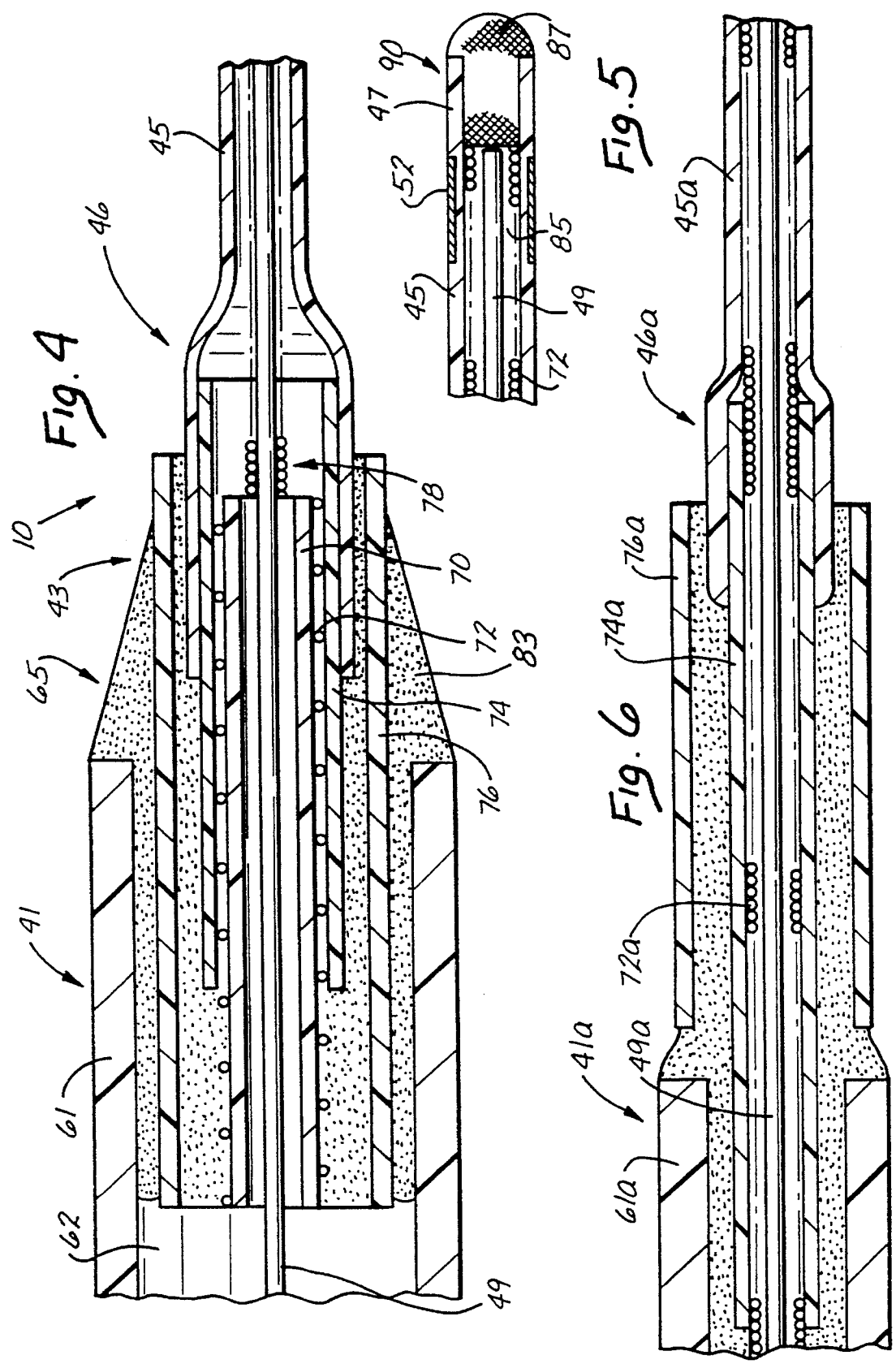

INTERNAL MAMMARY ARTERY CATHETER AND METHOD

This is a continuation, of application Ser. No. 07/962,975, filed Oct. 15, 1992, now abandoned.

BACKGROUND OF THE INVENTION

1. Field of the Invention

This invention relates generally to an apparatus for preparing autologous vessels for use in bypass surgery and more specifically to a catheter and method for dilating the internal mammary artery or other arterial conduits for such use.

2. Discussion of the Prior Art

Internal mammary arteries are vessels which originate at the subclavian arteries and deliver blood to the sternum and musculature of the chest wall. These arteries along with gastroepiploic and inferior epigastric arteries, are being used increasingly in cardiovascular bypass surgery.

It is the purpose of a bypass operations to provide a passage from a site of free flowing blood to a site distal to an occlusion in a coronary artery. In the past, saphenous veins have been harvested from the legs of patients and grafted to the coronary arteries for this purpose. One end of the graft has been attached to the aorta which provides the source of the blood, while the other end of the graft has been attached to the coronary artery distal of the occlusion. In this manner, blood from the aorta has bypassed the occlusion to feed the heart muscle.

The internal mammary artery (IMA) is the most frequently used arterial conduit for bypass grafting. In harvesting the IMA from the chest wall, the endothoracic facia is sometimes incised from around the IMA to sever the constricting bands of circumferential fascia. While the IMA remains attached to the subclavian artery, the mobilized end of the IMA pedicle is attached to the coronary artery. An obvious advantage over use of the saphenous vein is the fact that only one end of the IMA pedicle needs to be reattached while the other end can remain in its natural position.

Unfortunately, the IMA has characteristics which cause it to spasm or constrict in response to the trauma associated with mobilization. It has been found that mechanical circumferential stretching of the IMA tends to overcome this spasm leaving a relaxed, larger diameter conduit for bypass surgery.

In the past the stretching of the IMA to overcome spasm has been accomplished by introducing a balloon catheter into the IMA and then drawing the catheter and the inflated balloon through the entire length of the artery. While this has tended to overcome the spasm, it has also resulted in denudation or stripping of the arterial intimal cell layer, sometimes referred to as the intima. This internal layer comprises important endothelial cells which line the interior of the IMA and allow the IMA to regulate its own diameter. For this reason, it is desirable to overcome the spasm without injuring or remaining the intimal cell layer.

Procedures in the past have employed shear force gauges which measure the tensile force applied to the balloon catheter as the balloon is drawn through the IMA. While shear forces have been limited to approximately 30 grams, the intima is consistently damaged to an extent that has made this procedure clinically undesirable, and ultimately damaging to the long term performance of the graft in the patient.

SUMMARY OF THE INVENTION

In accordance with the present invention, a catheter is provided with a housing and a stylet extending through the housing to a distal end of the catheter. An elastomeric balloon is attached to the wire at a distal end of the catheter and attached to the housing at a proximal end of the catheter. This balloon may have an initial length of only one inch. However, as the stylet is moved distally, the balloon stretches axially to a length as great as six inches in one case. In this process, the axial stretching of the balloon causes it to neck down thereby facilitating insertion of the catheter into the IMA. Once the balloon is in place, it can be inflated to exert a radial pressure against the walls of the IMA. It has been found that this radial force, devoid of any shear force, is sufficient to overcome the spasm of the IMA and yet preserve the intimal cell layer.

When the IMA has been suitably stretched, the balloon can be deflated. Even though the balloon is deflated it remains axially stretched so that it maintains a reduced radial dimension. In this state, the diameter of the catheter and the balloon is less than the diameter of the IMA so the catheter can be retracted without exerting any shear force on the intima of the IMA.

In this procedure it is of particular advantage if the stylet is carried in a spring. In the absence of a spring, the stretched balloon may tend to grip the stylet preventing its further distal movement. This spring thus provides means for separating the stylet from the balloon to permit relative movement between the two as the stylet is inserted and the balloon is stretched axially.

These and other features and advantages of the invention will be more apparent with the discussion of preferred embodiments and reference to the associated drawings.

DESCRIPTION OF THE DRAWINGS

FIG. 4 is an axial cross-section view of one embodiment of a hub associated with the catheter of the present invention.

FIG. 5 is an axial cross-section view of the distal tip of the catheter of FIG. 4;

FIG. 6 is an axial cross-section view of another embodiment of the hub assembly associated with the catheter of the present invention;

FIG. 7 illustrates the catheter and the IMA in spasm;

FIG. 8 illustrates the stylet deployed and the balloon axially stretched prior to insertion in the IMA;

FIG. 9 illustrates the catheter with stretched balloon inserted in the spasmed vessel;

FIG. 10 illustrates the balloon inflated to enlarge the vessel;

FIG. 11 illustrates the balloon deflated with the vessel maintaining its enlarged state;

FIG. 12 illustrates the catheter withdrawn from the enlarged vessel; and

FIG. 13 illustrates the stylet retracted leaving the vessel in its enlarged state.

DESCRIPTION OF PREFERRED EMBODIMENTS AND BEST MODE OF THE INVENTION

Figure 1:
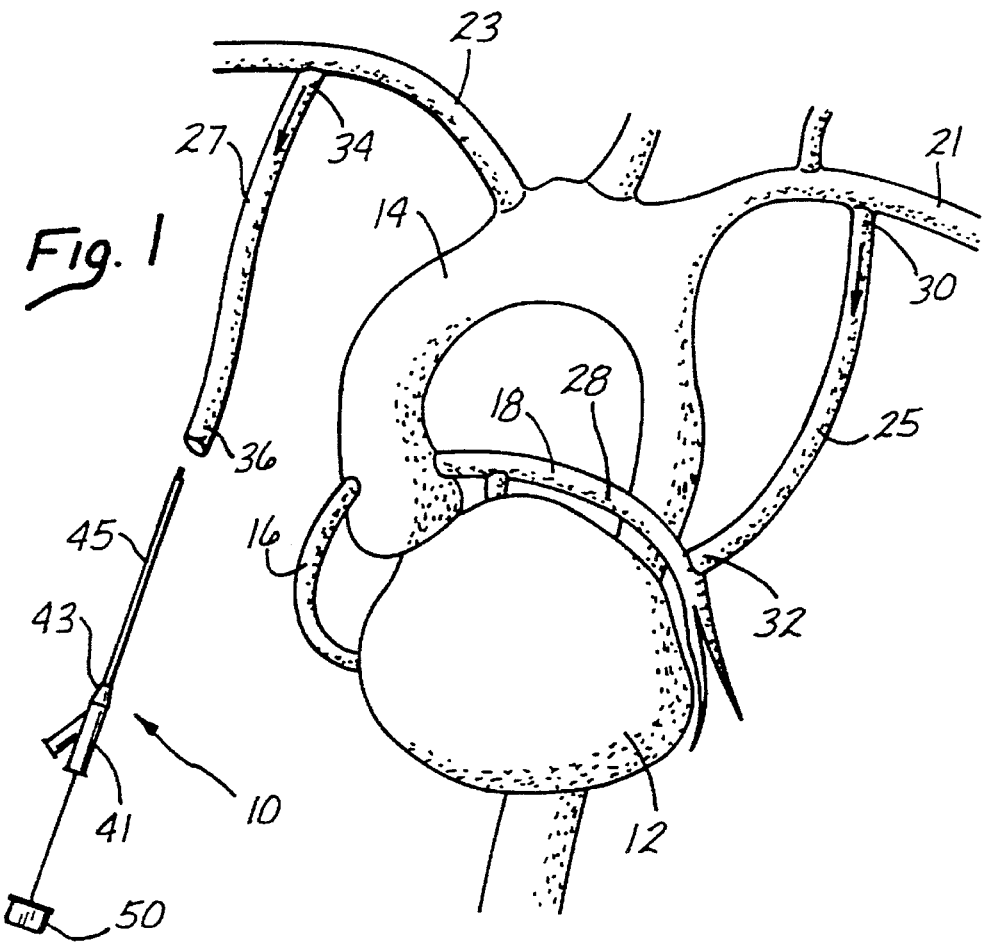
FIG. 1 is a schematic view of the heart and associated vasculature with an IMA catheter positioned to prepare the right IMA for coronary bypass surgery.

A catheter is illustrated in FIG. 1 and designated generally by the reference numeral 10. A heart 12 is also illustrated with a large arterial trunk, commonly referred to as the aorta 14, which conveys oxygenated blood to the entire circulatory system. As blood leaves the heart 12 and enters the aorta 14, it first encounters branches at a left coronary artery 16 and a right coronary artery 18. Subsequent branches from the aorta 14 include a left subclavian artery 21 and a right subclavian artery 23. Branching respectively from the subclavian arteries 21 and 23 are left and right internal mammary arteries respectively designated by the reference numerals 25 and 27. In the left internal mammary artery 25, the blood flows from a first end 30 to a second end 32. Similarly, in the right internal mammary artery 27 the blood flows from a first end 34 to a second end 36.

A coronary bypass operation is indicated when plaque formations in the coronary arteries, such as the arteries 16 and 18 block the flow of blood from the aorta 14 to distal regions of the heart. In the absence of oxygenated blood, the muscle of the heart 12 tends to deteriorate resulting in a heart attack. The plaque material in the artery tends to form a stenosis 28 which partially and perhaps totally occludes the coronary artery 18. It is the purpose of a coronary bypass operation to feed fresh blood around the stenosis 28 to the distal portions of the coronary arteries. This aids in maintaining the muscle of the heart and thereby avoids further damage to the heart 12.

The internal mammary arteries 25 and 27 normally supply oxygenated blood to the musculature of the chest wall. As illustrated in FIG. 1, the second ends 32 and 36 of the respective arteries 25 and 27 have been mobilized or removed from this musculature thereby adapting the arteries 25 and 27 to function as grafts in a coronary bypass operation. In this context, the arteries are commonly referred to as Internal Mammary Artery Grafts or IMAs. In FIG. 1 the second end 32 of the left IMA has already been attached to the left coronary artery 18. The right coronary artery 27 is illustrated at a time following its mobilization from the chest wall but prior to its attachment to the right coronary artery 16.

The internal mammary arteries are particularly adapted for use in coronary bypass surgery since they are of sufficient length that their first ends 30 and 34 can be left attached to the associated subclavian arteries 21 and 23. Only the second ends 32 and 36 of the arteries 25 and 27 need be mobilized to complete the bypass. In comparison to prior methods requiring the harvesting of the saphenous vein, the use of the internal mammary arteries for bypass provides much reduced trauma to the patient.

Mobilization of arterial conduits causes these vessels to spasm due to the trauma of mobilization. It has been found that stretching the walls of the vessel 25 and 27 outwardly tends to relieve this spasm leaving the artery 25, 27 with a larger lumen increasing the probability of long term patency.

A device particularly adapted for relieving the spasm of the artery 27 is the catheter 10. This catheter includes a hub 41, a stress relief section 43, and a balloon 45. The balloon 45 has a proximal end 46 with a fixed relationship to the hub 41 and a distal end 47.

A stylet 49 extends from a Luer cap 50 through the hub 41 and the stress relief section 43 to engage the distal end 47 of the balloon 45. At this location, the balloon is preferably sealed around the stylet 49 by a thread 52.

Figure 2:
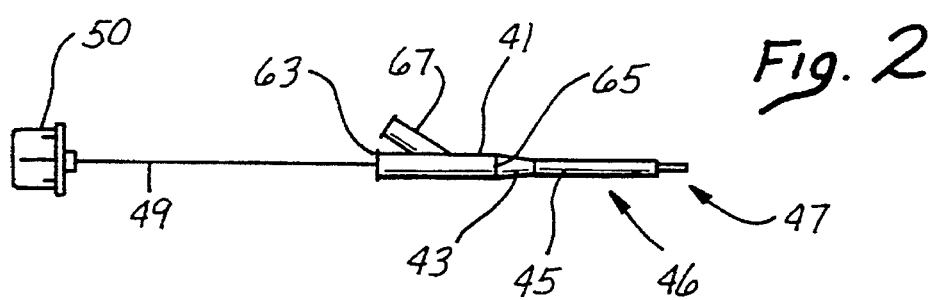
FIG. 2 is a side elevation view of the IMA catheter with the associated balloon in a natural, shortened state.
Figure 3:
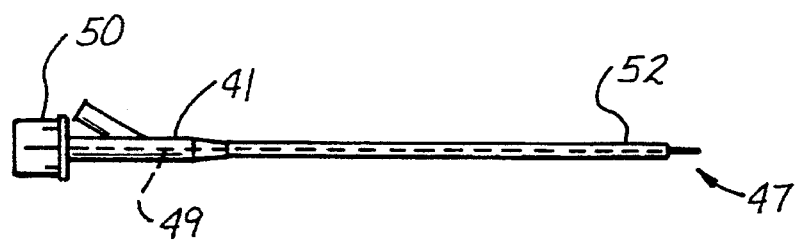
FIG. 3 is a side elevation view of the IMA catheter illustrated in FIG. 2 with the associated balloon in an axially elongated, radially contracted state.
Figure 7:
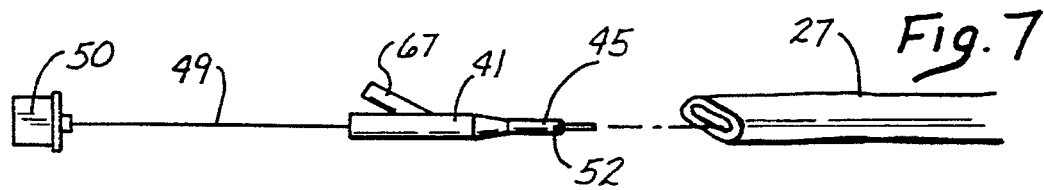
FIGS. 7–13 illustrate steps in a preferred method of the invention.
Figure 8:
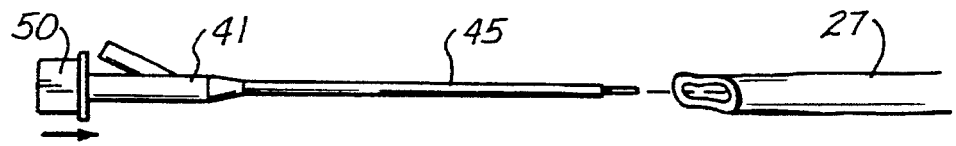
Figure 9:
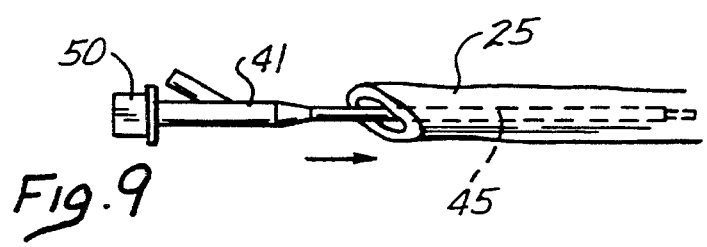
Figure 10:
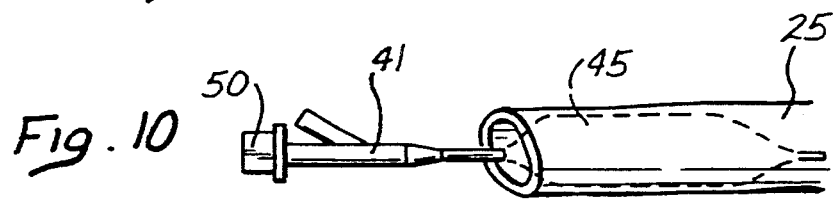
Figure 11:
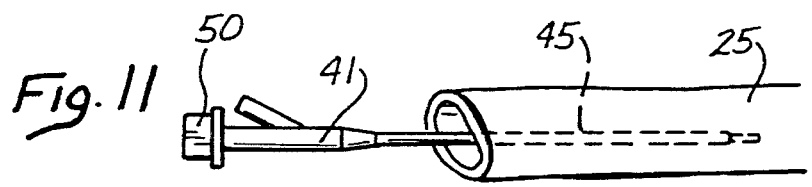
Figure 12:
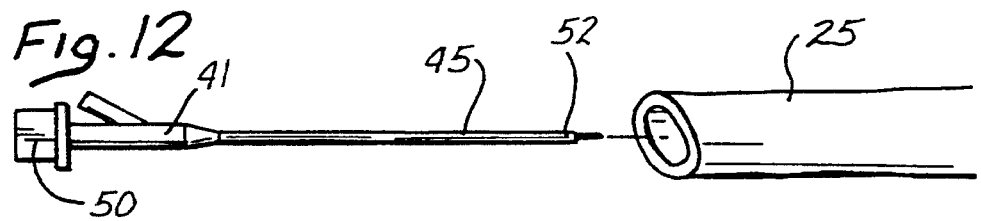
Figure 13:
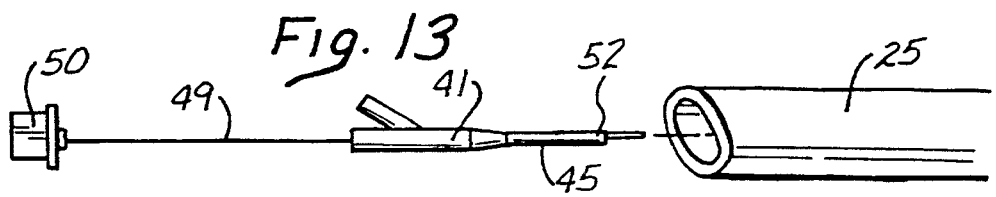

When the stylet 49 is advanced into the hub 41, the balloon 45 is stretched axially between the hub 41 and the distal end of the stylet 49. This stretches the balloon 45 from an axially compressed, radially expanded state illustrated in FIG. 2 to an axially stretched, radially contracted state as illustrated in FIG. 3. In the natural state, the balloon 45 may have a length such as 1.3 inches; in the expanded state, the balloon may have a length such as six inches.

The configuration of the catheter 10 can be better understood with reference to the cross-section views of FIGS. 4–6. In this embodiment, the hub comprises a standard "Y" hub having a housing or outer wall 61. This wall defines an interior cavity 62, an inlet port 63 at its proximal end, an outlet port 65 at its distal end, and a side port 67 best illustrated in FIG. 2.

The cavity 62 has a generally cylindrical configuration and the stylet 49 is disposed to extend along the axis of the cavity 62, into inlet port 63 and out of the exit port 65. Disposed concentrically outwardly of the stylet 49 at the exit port 65 are a spacer tube 70, a spring 72, a balloon support tube 74 and a stress relief tube 76.

In a process for manufacturing the catheter of FIG. 4, the stylet 49, tube 70, spring 72 and balloon support tube 74 are initially combined in a subassembly. The spacer tube 70 is positioned over the stylet 49 and the spring 72 is wound on the outer surface of the tube 70. At the distal end of the spacer tube 70, the diameter of the spring 72 is reduced at a step 78 to the diameter of the stylet 49. The winding of the spring 72 continues at this dimension to the distal end of the catheter 10.

The proximal end 46 of the balloon 45 is then stretched over this subassembly. Since it may be difficult to stretch the balloon 45 over the convolutions of the spring 72 at the "step" 78, it may be desirable to initially place the subassembly within the balloon support tube 74 and position the tube 74 so that it covers the distal end of the spacer tube 70. Then the proximal end 46 of the balloon 45 can be stretched over the distal end of the balloon support tube 74.

Once the balloon 45 has been mounted, the assembly can be disposed within the stress relief tube 76 which is positioned within the wall 62. In this embodiment of FIG. 4, the regions interior of the wall 61 and exterior of the spacer tube 70 can then be filled with a urethane adhesive to maintain these elements in their desired concentric relationship. The adhesive 83 should not contact the stylet 49 which is intended to move freely within the spacer tube 70 and the spring 72. The outer surface of the adhesive 83 can be tapered distally inwardly from the outer surface of the wall 61 to the distal end of the stress relief tube 76. This tapered adhesive as well as the tube 76 provide a gradually reduced diameter for the catheter 10 which aids in relieving bending stresses which may be encountered. With the adhesive 83 positioned as illustrated, the cavity 62 communicates through the spacer tube 70 with the regions interior of the tube 45.

A further embodiment of the invention, illustrated in FIG. 6, provides a narrower configuration for the hub 41. The elements illustrated in this embodiment which have characteristics similar to those previously discussed are designated with the same reference numerals followed by the lower case letter "a".

The embodiment of FIG. 6 is similar to that of FIG. 4 except that the stress relief tube 76a is not disposed within the outer wall 61a of the hub 41a. This permits the outer wall 61a to have a reduced diameter. The spacer tube 70 of the FIG. 4 embodiment is eliminated in this case and the spring 72a is wound over the stylet 49a without a change in diameter. In this embodiment, the balloon support tube 74a is also positioned outwardly of the spring 72a and adapted to receive the proximal end 46a of the spring 45a. The adhesive 83a is disposed outwardly of the spring 72a and the balloon support tube 74a, and inwardly of the wall 61a and the strain relief tube 76a.

Both of these embodiments of the catheter 10 can have a distal end such as that illustrated in FIG. 5. At the distal end it is important that the balloon 45 be provided with a fixed relationship with the stylet 49. This can be accomplished with the threads 52 which are tightly wound around the balloon 45 compressing the balloon against the spring 72. A cyanoacrylate adhesive 85, or other suitable bonding means, can be disposed between the spring 72 and the stylet 49 to achieve this fixed relationship. This adhesive 85 is preferably provided proximally of the distal end 47 of the balloon 45 leaving a cavity which can then be filled with a UV plug 87 of material, such as an activated urethane adhesive, which provides the catheter with a flexible distal tip 90.

It is of particular importance that the spring 72 is disposed between the stylet 49 and the interior surface of the balloon 45. Since this balloon 45 is required to extend to as much as six times its normal length, it will tend to contract radially inwardly as it is axially extended. It has been found that in the absence of the spring or other means for slidably separating the stylet 49 from the balloon 45, that the balloon will eventually grip the stylet and prevent any further distal movement of the stylet 49 or the balloon 45. With the spring 72 positioned between the balloon 45 and the stylet 49, the convolutions of the spring 72 tend to grip the radially contracting balloon 45 and aid in the extension of the balloon as these convolutions separate. Interiorly of the spring 72, the convolutions provide a surface which offers substantially no resistance to the axial movement of the stylet 49.

A method of the present invention is illustrated in FIGS. 7–13. As noted, when the internal mammary artery 27 is initially mobilized it tends to spasm and contract radially. It is this state which is to be overcome by stretching the artery 27. Initially the catheter 10 is positioned with the stylet 49 retracted and the balloon axially contracted and radially enlarged. From this normal state, the Luer cap 50 can be moved in the direction of the hub 41 advancing the stylet 49 to move the distal tip 90 away from the hub 41. This stretches the balloon 45 to its axially extended, radially contracted state. The catheter 10 can be locked in this state by screwing the Luer cap 50 onto the inlet port 63 of the hub 41.

At this point, the catheter 10 is ready to be inserted into the spasmed artery 27. When the catheter in the extended state is positioned within the artery 27, the balloon 45 can be inflated by introducing air or fluid into the side port 67. In this important step, the balloon exerts a force on the artery 27 which has only radial components. In other words, the balloon 45 moves radially outwardly opposing the spasm and stretching the vessel 27 outwardly but not longitudinally. There is no axial movement of the catheter 10 and particularly the balloon 45 during this inflation step. As a result, the intima is merely pressed against the inner wall of the vessel 27 and is not subjected to any damaging shear stresses.

When the artery 27 has been expanded and the spasm has been overcome, the balloon 45 can be deflated and the catheter 10 withdrawn axially from the patent artery 27. This will leave the artery 27 in a patent enlarged configuration ready for attachment to the associated coronary artery.

Although the present invention is not material dependent, in a preferred embodiment of the concept, the strain relief tube 76 is formed from polyvinylchloride while the spacer tube 70 and the balloon support tube 74 are formed from a polyamide material. The adhesives 83 and 87 in this embodiment are UV activated urethanes while the adhesive 85 is preferably a cyanoacrylate. While these materials combine in a preferred embodiment of the invention, any one of the foregoing elements can be formed from a different material all within the scope of the present invention.

It will also be apparent that various elements of the catheter 10 can be replaced with similar structure. Particularly the spring 72 might be replaced by a tubular structure providing the necessary separation between the balloon 45 and the stylet 49. The balloon 45 could also be formed of any suitable material providing the desired elastomeric characteristics for the extended longitudinal expansion contemplated by the present invention.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A method for preparing a body conduit for attachment to a coronary artery in bypass surgery, the conduit having a diameter and a length, the method comprising the steps of:

a) inserting into the conduit a catheter having a distal end and an elongate contractible expansion member disposed at the distal end of the catheter, the member having a diameter and a length, and being insertable into the conduit in a contracted state wherein the diameter of the member is less than the diameter of the conduit;

b) expanding the member within the conduit, while minimizing axial movement of the catheter with respect to the conduit, to thereby produce a radial force along the length of the conduit which is substantially devoid of any shear force components and has a magnitude which is sufficient to dilate the conduit;

c) holding the catheter in a fixed axial position at all times while the member is expanded;

d) radially contracting the member without exerting any shear force on the conduit;

e) withdrawing the catheter and the member from the dilated conduit with the member in the contracted state; and then f) attaching the dilated conduit to the coronary artery.

2. The method recited in claim 1 wherein the arterial conduit is an internal mammary artery having a first end attached to a first artery and a second end attached to a second artery, the method further comprising the steps of:

detaching the second end of the internal mammary artery from the second artery leaving the first end of the internal mammary artery attached to the first artery;

during the inserting step, inserting the catheter into the second end of the internal mammary artery; and during the attaching step, attaching the second end of the internal mammary artery to the coronary artery.

3. The method recited in claim 1 wherein:

the contractible expansion member is a balloon;

the expanding step includes the step of inflating the balloon; and the contracting step includes the step of deflating the balloon.

4. The method recited in claim 3 wherein the conduit has an intimal lining and the inflating step includes the step of:

contacting the intimal lining with the balloon.

5. A method for relieving spasm in an body conduit having an axis, a diameter and a length, the conduit including an intimal lining extending along the entire length of the conduit, the method comprising the steps of:

providing a catheter having a distal end;

providing an inflatable elongate balloon at the distal end of the catheter, the balloon having a diameter and a length, and properties including a deflated state wherein the pressure within the balloon is generally equal to the pressure outside the balloon and the diameter of the balloon is less than the diameter of the conduit;

inserting the balloon of the catheter into the conduit with the balloon in the deflated state in order to avoid substantially any shear force on the intimal lining;

inflating the balloon to relieve the spasm in the arterial conduit;

during the inflating step exerting a force on the intimal lining of the conduit, the force generally including only radial force components;

holding the catheter in a fixed axial position at all times while the balloon is inflated;

deflating the balloon to place the balloon in the deflated state;

moving the catheter axially within the conduit; and during the moving step maintaining the balloon in the deflated state in order to avoid substantially any shear force on the intimal lining of the conduit.

6. The method recited in claim 5 wherein the moving step comprises the step of withdrawing the catheter axially from the conduit with the balloon in the deflated state.

7. The method recited in claim 5 wherein prior to the inserting step the method further comprises the step of providing the catheter with a stylet for releasably locking the balloon in an axially extended, radially contracted state.

8. The method recited in claim 7 further comprising prior to each of the steps of inserting and moving, releasably locking the balloon in the axially extended, radially contracted state.

9. A method for preparing a body conduit for attachment to a coronary artery in bypass surgery, the conduit having an intimal lining with beneficial properties which are degraded when the lining is subjected to shear forces above a predetermined magnitude, the conduit having a diameter and a length, and the method comprising the steps of:

providing a catheter having a distal end and an elongate balloon disposed at the distal end of the catheter, the balloon being inflatable from a deflated state wherein the diameter of the balloon is less than the diameter of the conduit;

moving the catheter axially into the conduit until the catheter is disposed at an operative site in the conduit;

ceasing axial movement of the catheter at the operative site;

dilating the conduit by inflating the balloon with the catheter at the operative site to expand the balloon radially outwardly against the intimal lining of the conduit without subjecting the intimal lining to any shear forces greater than the predetermined magnitude;

holding the catheter in a fixed axial position at all times while the balloon is in an expanded state;

deflating the balloon to place the balloon in the deflated state at the operative site; and withdrawing the catheter and the balloon from the conduit with the balloon in the deflated state in order to avoid any shear force on the intimal lining which is greater than the predetermined magnitude.

\* \* \* \* \*